US008936768B2

(12) United States Patent
Timken et al.

(10) Patent No.: US 8,936,768 B2
(45) Date of Patent: *Jan. 20, 2015

(54) ALKYLATION PROCESS UNIT FOR PRODUCING HIGH QUALITY GASOLINE BLENDING COMPONENTS IN TWO MODES

(75) Inventors: Hye Kyung Cho Timken, Albany, CA (US); Shawn Shlomo Winter, Salt Lake City, UT (US); Howard Steven Lacheen, Richmond, CA (US); Sven Ivar Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/551,904

(22) Filed: Jul. 18, 2012

(65) Prior Publication Data

US 2012/0282150 A1    Nov. 8, 2012

Related U.S. Application Data

(60) Division of application No. 12/725,987, filed on Mar. 17, 2010, now Pat. No. 8,895,794, and a continuation of application No. 12/726,009, filed on Mar. 17, 2010, now Pat. No. 8,487,154, and a continuation of application No. 12/725,969, filed on Mar. 17, 2010, now Pat. No. 8,455,708.

(51) Int. Cl.
*B01J 8/08* (2006.01)
*C10G 29/20* (2006.01)
*C07C 2/58* (2006.01)

(52) U.S. Cl.
CPC ........... *C10G 29/205* (2013.01); *C07C 2/58* (2013.01); *C07C 2527/125* (2013.01); *C07C 2531/02* (2013.01); *C10G 2400/02* (2013.01); *C10G 2300/20* (2013.01); *C10G 2300/202* (2013.01); *C10G 2300/305* (2013.01)
USPC ........................................... 422/610; 422/187

(58) Field of Classification Search
CPC .......................................................... B01J 8/08
USPC .................................................. 422/102, 187
See application file for complete search history.

(56) References Cited

U.S. PATENT DOCUMENTS

| | | | |
|---|---|---|---|
| 2,983,774 A * | 5/1961 | Thompson | 585/372 |
| 6,194,625 B1 * | 2/2001 | Graves et al. | 585/313 |
| 7,432,408 B2 | 10/2008 | Timken et al. | |
| 7,432,409 B2 | 10/2008 | Elomari et al. | |
| 7,495,144 B2 | 2/2009 | Elomari | |
| 7,553,999 B2 | 6/2009 | Elomari et al. | |
| 7,569,740 B2 | 8/2009 | Elomari | |
| 7,572,943 B2 | 8/2009 | Elomari et al. | |
| 7,572,944 B2 | 8/2009 | Elomari et al. | |
| 7,576,252 B2 | 8/2009 | Elomari et al. | |
| 7,615,598 B2 | 11/2009 | Hope et al. | |
| 7,723,556 B2 | 5/2010 | Elomari et al. | |
| 7,732,654 B2 | 6/2010 | Elomari et al. | |
| 7,919,663 B2 | 4/2011 | Hommeltoft et al. | |

(Continued)

*Primary Examiner* — In Suk Bullock
*Assistant Examiner* — Sharon Pregler
(74) *Attorney, Agent, or Firm* — Susan M. Abernathy

(57) ABSTRACT

We provide an alkylation process unit, comprising: a control system connected to an alkylation reactor, that enables the alkylation reactor to operate in both an alkylate mode that produces a gasoline blending component having a RON of 90 or higher and in a distillate mode that produces a second gasoline blending component having a RON of 85 or higher.

19 Claims, 1 Drawing Sheet

Flexible Production of Alkylate Gasoline and Distillate with Ionic Liquid Catalyst

(56) References Cited

U.S. PATENT DOCUMENTS

| | | |
|---|---|---|
| 7,923,594 B2 | 4/2011 | Hommeltoft |
| 7,988,747 B2 | 8/2011 | Lacheen et al. |
| 8,070,939 B2 | 12/2011 | Hommeltoft |
| 8,124,821 B2 | 2/2012 | Elomari |
| 8,178,739 B2 | 5/2012 | Elomari et al. |
| 2006/0131209 A1* | 6/2006 | Timken et al. ............ 208/16 |
| 2007/0142213 A1* | 6/2007 | Elomari et al. ............ 502/53 |
| 2007/0142690 A1 | 6/2007 | Elomari |
| 2007/0249486 A1 | 10/2007 | Elomari et al. |
| 2010/0152027 A1 | 6/2010 | Lacheen et al. |
| 2010/0152506 A1 | 6/2010 | Hommeltoft et al. |
| 2010/0298620 A1 | 11/2010 | Hommeltoft |
| 2011/0105811 A1 | 5/2011 | O'Rear et al. |

* cited by examiner

Flexible Production of Alkylate Gasoline and Distillate with Ionic Liquid Catalyst
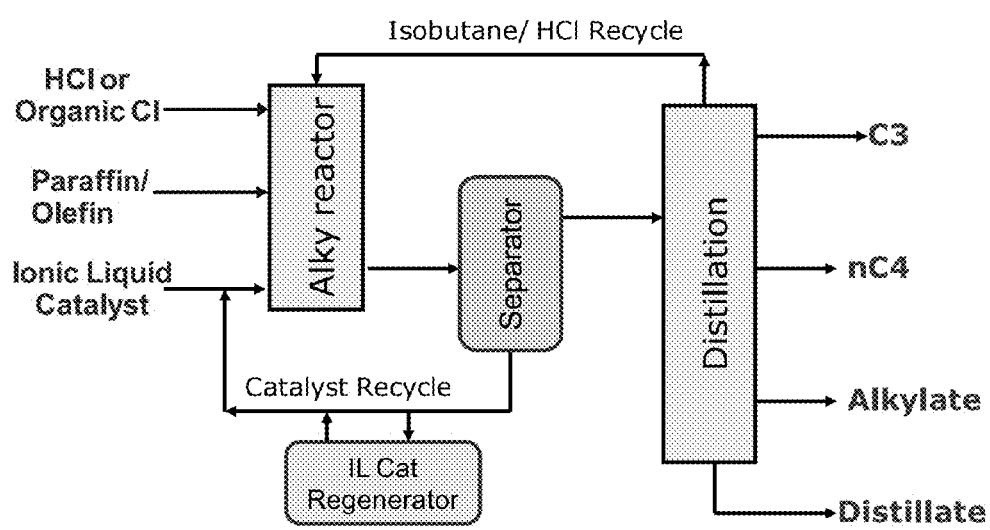

ALKYLATION PROCESS UNIT FOR PRODUCING HIGH QUALITY GASOLINE BLENDING COMPONENTS IN TWO MODES

This application is a divisional of U.S. patent application Ser. No. 12/725,987, published as US 2011-0230692 A1, filed Mar. 17, 2010, in Group Art Unit 1772; and herein incorporated in its entirety. This application claims priority to U.S. patent application Ser. No. 12/725,969, published as US 2011-0226664 A1, filed Mar. 17, 2010; herein incorporated in its entirety. This application also claims priority to U.S. patent application Ser. No. 12/726,009, published as US 2011-0226669 A1, filed Mar. 17, 2010; herein incorporated in its entirety.

TECHNICAL FIELD

This application is directed to a process for producing high quality gasoline blending components and a distillate and to an alkylation process unit for producing high quality gasoline blending components and a distillate.

SUMMARY

This application provides a process for producing high quality gasoline blending components, comprising:

a) operating an alkylation reactor in an alkylate mode wherein a gasoline blending component is made having a RON of 90 or higher; and b) operating the alkylation reactor in a distillate mode wherein a second gasoline blending component and a distillate product is made, and wherein the second gasoline blending component has a RON of 85 or higher.

This application also provides an alkylation process unit, comprising: a control system connected to an alkylation reactor that enables the alkylation reactor to operate in both an alkylate mode that produces a gasoline blending component having a RON of 90 or higher and in a distillate mode that produces a second gasoline blending component having a RON of 85 or higher.

BRIEF DESCRIPTION OF THE DRAWING

FIG. 1 is a process flow diagram of an embodiment showing flexible production of alkylate gasoline and distillate with an ionic liquid catalyst.

DETAILED DESCRIPTION

The alkylation reactor is designed to operate in both an alkylate mode and a distillate mode. In the alkylate mode, the reactor produces a higher amount of $C_5^+$ hydrocarbons boiling at 430° F. (221.1 degree Celsius) or below. In the distillate mode the alkylation reactor produces a higher amount of $C_5^+$ hydrocarbons boiling above 280° F. (137.8 degree Celsius). In one embodiment, greater than 50 wt % of a $C_5^+$ hydrocarbon stream produced in the alkylation reactor in the alkylate mode boil at 280° F. (137.8 degree Celsius) or below, and greater than 50 wt % of a $C_5^+$ hydrocarbon stream produced in the alkylation reactor in the distillate mode boil above 280° F. (137.8 degree Celsius). An advantage of the alkylation reactor is that both a gasoline blending component having a RON of 90 or higher and a second gasoline blending component having a RON of 85 or higher are made during both modes of operation. Additionally, a distillate product is made while the alkylation reactor is operating in the distillate mode.

The "gasoline blending component" can be either a gasoline or a naphtha hydrocarbon product suitable for blending into a gasoline. "Gasoline" is a liquid hydrocarbon used as a fuel in internal combustion engines. In the context of this disclosure, "distillate" is a liquid hydrocarbon having a boiling range from about 280° F. and higher. It can comprise one or both of "light distillate" and "heavy distillate." "Light distillate" is a liquid hydrocarbon having a boiling range from about 280° F. to about 500° F., and "heavy distillate" is a liquid hydrocarbon having a boiling range from about 500° F. and higher. The boiling range is the 10 vol % boiling to the final boiling point (99.5 vol %), inclusive of the end points, as measured by ASTM D2887-06a and ASTM D 6352-04.

In other embodiments, the gasoline blending component has a RON of 90 or higher, or the second gasoline blending component has a RON of 85 or higher. In some embodiments, both the gasoline blending component and the second gasoline blending component have a RON of 90 or higher. The Research-method octane number (RON) is determined using ASTM D 2699-07a. RON employs the standard Cooperative Fuel Research (CFR) knock-test engine.

In one embodiment, the gasoline blending component, the second gasoline blending component, the distillate product, or combinations thereof, have low sulfur. The level of sulfur can be less than 25 wppm, less than 20 wppm, less than 10 wppm, or less than 5 wppm. For example, the gasoline blending component, the light distillate, and the heavy distillate can all have less than 25 wppm sulfur, less than 20 wppm sulfur, less than 10 wppm sulfur, or even less than 5 wppm sulfur, when the alkylation reactor is operating in the distillate mode.

In general, the alkylation reactor comprises an alkylation catalyst. In one embodiment the alkylation catalyst is an acidic ionic liquid catalyst.

The alkylation conditions in the alkylation reactor are selected to provide the desired product yields and quality. The alkylation reaction in the alkylation reactor is generally carried out in a liquid hydrocarbon phase, in a batch system, a semi-batch system, or a continuous system. Catalyst volume in the alkylation reactor is in the range of 1 vol % to 80 vol %, for example from 2 vol % to 70 vol %, from 3 vol % to 50 vol %, or from 5 vol % to 25 vol %. In some embodiments, vigorous mixing can be used to provide good contact between the reactants and the catalyst. The alkylation reaction temperature can be in the range from −40° C. to 150° C., such as −20° C. to 100° C., or −15° C. to 50° C. The pressure can be in the range from atmospheric pressure to 8000 kPa. In one embodiment the pressure is kept at a high enough level to keep the reactants in the liquid phase. The residence time of reactants in the reactor can be in the range of a second to 60 hours.

The molar ratio of isoparaffin to olefin in the alkylation reactor can vary over a broad range. Generally the molar ratio of isoparaffin to olefin is in the range of from 0.5:1 to 100:1. For example, in different embodiments the molar ratio of isoparaffin to olefin is from 1:1 to 50:1, 1.1:1 to 10:1, or 1.1:1 to 20:1. Lower isoparaffin to olefin molar ratios will tend to produce a higher yield of higher molecular weight alkylate products, and thus can be selected when operating the alkylation reactor in the distillate mode.

In one embodiment one or more process conditions in the alkylation reactor are adjusted between operating in the alkylate mode and operating in the distillate mode. In some embodiments, the alkylation reactor can switch back and forth from operating in the alkylate mode to operating in the distillate mode. In some embodiments, the control system connected to the alkylation reactor switches back and forth from enabling the alkylation reactor to operate in the alkylate mode to enabling the alkylation reactor to operate in the distillate mode.

The adjusting of the one or more process conditions in the alkylation reactor can be done by controlling a level of a conjunct polymer in an alkylation catalyst, by controlling a level of a halide containing additive in the alkylation reactor, by changing a ratio of isoparaffin to olefin in a feed to the alkylation reactor, by changing a reaction temperature, or by a combination thereof. In general, the higher the level of the conjunct polymer in the alkylation reactor the higher the level of the $C_5^+$ hydrocarbon stream from the alkylation reactor that boils above 280° F. (137.8 degree Celsius).

In one embodiment the level of the conjunct polymer in the alkylation catalyst is at a lower level when the alkylation reactor is operating in the alkylate mode. The lower level, for example, can be less than 20 wt %, less than 15 wt %, less than 10 wt %, from between 5 wt % and 10 wt %, from 0 to 15 wt %, or from 0 to 10 wt %. The level is adjusted by controlling the level of the conjunct polymer in the alkylation catalyst to a higher level in the distillate mode, for example, above 5 wt %, above 10 wt %, above 15 wt %, above 20 wt %, above 30 wt %, or above 40 wt %. The level can be adjusted back and forth from the lower level to the higher level to switch back and forth from operating in the alkylate mode to operating in the distillate mode.

In one embodiment the level of the halide containing additive is adjusted upward to boost the overall acidity of conditions in the process unit to increase the total wt % of the $C_5^+$ hydrocarbons. The halide containing additive can be a hydrogen halide, an organic halide, and combinations thereof. In one embodiment, the halide containing additive can be a Bronsted acid, for example, HCl, HBr, and trifluoromethanesulfonic acid. Adjusting the level of the halide containing additive can be used to switch back and forth between operating in the alkylate mode and the distillate mode. By adjusting the level of the halide containing additive to a lower level a higher level of $C_5^+$ hydrocarbons in the process unit boil above 280° F. (137.8 degree Celsius). By adjusting the level of the halide containing additive to a higher level, a higher level of $C_5^+$ hydrocarbons in the process unit boils at 280° F. (137.8 degree Celsius) or below. The level of the halide containing additive can be adjusted by varying the molar ratio of an olefin to the halide containing additive in a feed to the alkylation reactor. Processes for adjusting the level of a halide containing additive to shift selectivity towards heavier products is taught in US Patent Publication Number US20100025292.

In other embodiments the adjusting is done by changing a ratio of isoparaffin to olefin in a feed to the alkylation reactor. In general, lowering the molar ratio of isoparaffin to olefin in the feed will produce a higher level of $C_5^+$ hydrocarbons in the process unit that boil above 280° F. (137.8 degree Celsius). In one embodiment, the molar ratio of isoparaffin to olefin in the feed while operating the alkylation reactor in the alkylate mode is from 4:1 to 100:1, such as from 4:1 to 50:1, or from 4:1 to 20:1; and the molar ratio of isoparaffin to olefin in the feed while operating the alkylation reactor in the distillate mode is a lower molar ratio from that used during the alkylate mode, from 0.25:1 to 25:1, such as from 0.25:1 to 20:1, or 0.25:1 to 10:1. In a different embodiment the molar ratio of isoparaffin to olefin in the feed is approximately the same while operating in both the alkylate mode and the distillate mode. In one embodiment, the control system connected to the alkylation reactor adjusts the molar ratio of isoparaffin to olefin by controlling a level of isoparaffin recycled to the alkylation reactor. In some embodiments, the control system connected to the alkylation reactor adjusts both the molar ratio of isoparaffin to olefin by controlling a level of isoparaffin recycled to the alkylation reactor and the level of HCl being recycled to the alkylation reactor in a common recycle stream.

In another embodiment, the adjusting is done by changing the reaction temperature. In general, increasing the reaction temperature will produce a higher level of $C_5^+$ hydrocarbons in the process unit that boil above 280° F. (137.8 degree Celsius). In one embodiment, the reaction temperature while operating the process unit in the alkylate mode is from −40° C. to 100° C.; and the reaction temperature while operating the process unit in the distillate mode is a higher temperature, from 0° C. to 200° C. In a different embodiment the reaction temperature is approximately the same while operating in both the alkylate mode and the distillate mode.

The process can additionally comprise adjusting one or more process conditions in the alkylation reactor after operating in the distillate mode to return to operating the process unit in the alkylate mode. This can be advantageous when there is a shift in market demand, or an increased value for products produced during one of the modes.

In one embodiment, when operating the alkylation reactor in the alkylate mode, the process generally produces greater than 50 wt % of a $C_5^+$ hydrocarbon stream from the process unit that boils at 280° F. (137.8 degree Celsius) or below. In other embodiments, the process can produce greater than 55 wt %, greater than 60 wt %, greater than 70 wt %, greater than 80 wt %, or greater than 90 wt % of a $C_5^+$ hydrocarbon stream from the process unit that boils at 280° F. (137.8 degree Celsius) or below while operating in the alkylate mode.

In one embodiment, when operating the alkylation reactor in the distillate mode, the process generally produces greater than 50 wt % of a $C_5^+$ hydrocarbon stream from the process unit that boils above 280° F. (137.8 degree Celsius). In other embodiments, the process can produce greater than 55 wt %, greater than 60 wt %, greater than 70 wt %, greater than 80 wt %, or greater than 90 wt % of a $C_5$+ hydrocarbon stream from the process unit that boils above 280° F. (137.8 degree Celsius).

The alkylation reactor comprises an alkylation catalyst. In one embodiment, the alkylation catalyst is an acidic ionic liquid catalyst.

In one embodiment the operating of the alkylation reactor in an alkylate mode comprises alkylating using an acidic ionic liquid catalyst. Examples of alkylation processes for making alkylate gasoline with low volatility and high octane number are described in U.S. Pat. No. 7,432,408 and US Patent Publication Number US20100025292. Other processes for alkylating using an acidic ionic liquid catalyst are described in U.S. Pat. Nos. 7,432,409; 7,495,144; 7,553,999; US Patent Publication Numbers US20090107032 and US20100025296; and patent application Ser. Nos. 12/335,476 and 12/335,487, both filed on Dec. 15, 2008.

In another embodiment, the operating of the alkylation reactor in a distillate mode comprises alkylating and oligomerizing using an acidic ionic liquid catalyst. Examples of processes to make higher boiling hydrocarbons are described in U.S. Pat. Nos. 7,572,943; 7,569,740; 7,576,252; 7,572,944; and US Patent Publication Numbers US20090306444, US 20090270667, US20090270666, and US20100025292; U.S. patent application Ser. Nos. 12/233,481, filed on Sep. 18, 2008, 12/538,738, filed on Aug. 10, 2009, 12/538,746, filed Aug. 10, 2009, and 12/610,010, filed Oct. 30, 2009.

The acidic ionic liquid catalyst used in the operating of the alkylation reactor in the alkylate mode can be the same or different from the acidic ionic liquid catalyst used in the operating of the alkylating reactor in the distillate mode. The acidic ionic liquid catalyst is composed of at least two components which form a complex. The acidic ionic liquid catalyst comprises a first component and a second component. The first component of the acidic ionic liquid catalyst can comprise a Lewis Acid selected from components such as Lewis Acidic compounds of Group 13 metals, including aluminum halides, alkyl aluminum halide, gallium halide, and alkyl gallium halide (see International Union of Pure and Applied Chemistry (IUPAC), version3, October 2005, for Group 13 metals of the periodic table). Other Lewis Acidic compounds, in addition to those of Group 13 metals, can also be used. In one embodiment the first component is aluminum halide or alkyl aluminum halide. For example, aluminum trichloride can be the first component of the acidic ionic liquid catalyst.

The second component making up the acidic ionic liquid catalyst is an organic salt or mixture of salts. These salts can be characterized by the general formula Q+A−, wherein Q+ is an ammonium, phosphonium, boronium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the acidic ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the acidic ionic liquid catalyst can be an acidic haloaluminate ionic liquid, such as an alkyl substituted pyridinium chloroaluminate or an alkyl substituted imidazolium chloroaluminate of the general formulas A and B, respectively.

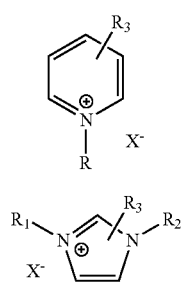

In the formulas A and B; R, $R_1$, $R_2$, and $R_3$ are H, methyl, ethyl, propyl, butyl, pentyl or hexyl group, X is a chloroaluminate. In the formulas A and B, R, $R_1$, $R_2$, and $R_3$ may or may not be the same. In one embodiment the acidic ionic liquid catalyst is N-butylpyridinium chloroaluminate.

In another embodiment the acidic ionic liquid catalyst can have the general formula RR'R" N H$^+$Al$_2$Cl$_7^-$, wherein N is a nitrogen containing group, and wherein R,R', and R" are alkyl groups containing 1 to 12 carbons, and where R,R', and R" may or may not be the same.

The presence of the first component should give the acidic ionic liquid a Lewis or Franklin acidic character. Generally, the greater the mole ratio of the first component to the second component, the greater is the acidity of the acidic ionic liquid catalyst.

In one embodiment, the acidic ionic liquid catalyst is mixed in the alkylation reactor with a hydrogen halide or an organic halide. The hydrogen halide or organic halide can boost the overall acidity and change the selectivity of the acidic ionic liquid catalyst. The organic halide can be an alkyl halide. The alkyl halides that can be used include alkyl bromides, alkyl chlorides, alkyl iodides, and mixtures thereof. A variety of alkyl halides can be used. Alkyl halide derivatives of the isoparaffins or the olefins that comprise the feed streams in the alkylation process are good choices. Such alkyl halides include, but are not limited to, iospentyl halides, isobutyl halides, butyl halides, propyl halides and ethyl halides. Other alkyl chlorides or halides having from 1 to 8 carbon atoms can be also used. The alkyl halides can be used alone or in combination. The use of alkyl halides to promote hydrocarbon conversion by acidic ionic liquid catalysts is taught in U.S. Pat. No. 7,495,144 and in U.S. patent application Ser. No. 12/468,750, filed May 19, 2009.

It is believed that the alkyl halide decomposes under hydrocarbon conversion conditions to liberate Bronsted acids or hydrogen halides, such as hydrochloric acid (HCl) or hydrobromic acid (HBr). These Bronsted acids or hydrogen halides promote the hydrocarbon conversion reaction. In one embodiment the halide in the hydrogen halide or alkyl halide is the same as a halide component of the acidic ionic liquid catalyst. In one embodiment the alkyl halide is an alkyl chloride, for example t-butyl chloride. A hydrogen chloride or an alkyl chloride can be used advantageously, for example, when the acidic ionic liquid catalyst is a chloroaluminate.

The alkylation reactor can be switched back and forth from operating in the alkylate mode to the distillate mode quickly, which is advantageous when market demands or product pricing swing rapidly. For example, the time between operating in the alkylate mode and operating in the distillate mode can be a week or less. In one embodiment, the alkylation reactor can switch back and forth within a month, within two weeks or less, within a week or less, within 5 days or less, within 4 days or less, within 3 days or less, within 2 days or less, or within 1 day or less.

In some embodiments, the gasoline blending component, the second gasoline blending component, or both, can be a low volatility gasoline blending component having a Reid Vapor Pressure of 7.0 psi (4.827e+004 newtons/square meter) or less. In one embodiment the gasoline blending component, the second gasoline blending component, or both, has a Reid Vapor Pressure (RVP) less than 4.0 psi (2.758e+004 newtons/square meter). In other embodiments the gasoline blending component or the second gasoline blending component has a RVP of 2.8 psi (1.931e+004 newtons/square meter) or less, or less than the amount defined by the equation: RVP=−0.035× (50 vol % boiling point, ° C.)+5.8, in psi. The chart of this equation is shown in FIG. 1 in US Patent Publication Number US 20100025292.

In one embodiment, the alkylation process unit comprises a control system connected to the alkylation reactor that enables the alkylation reactor to operate in both an alkylate mode that produces a gasoline blending component having a RON of 90 or higher and in a distillate mode that produces a second gasoline blending component having a RON of 85 or higher. The control system can adjust one or more process conditions, as described previously. In one embodiment the control system controls both a level of a conjunct polymer in an ionic liquid catalyst in the alkylation reactor and a level of a halide containing additive in the alkylation reactor. In another embodiment the control system controls a level of a conjunct polymer in an ionic liquid catalyst in the alkylation reactor, a molar ratio of isoparaffin to olefin in the alkylation reactor, and a level of a halide containing additive in the alkylation reactor.

In one embodiment, the control system controls a level of a conjunct polymer in an acidic ionic liquid catalyst in the alkylation reactor. The term conjunct polymer was first used by Pines and Ipatieff to distinguish these polymeric molecules from the usual polymers. Unlike typical polymers, conjunct polymers are polyunsaturated cyclic, polycyclic and acyclic molecules formed by concurrent acid-catalyzed reactions including, among others, polymerization, alkylation, cyclization, and hydride transfer reactions. Conjunct polymers consist of an unsaturated intricate network of molecules that can include one or a combination of 4-, 5-, 6- and 7-membered rings and some aromatic entities in their skeletons. Some examples of the likely polymeric species were reported by Miron et al. (Journal of Chemical and Engineernig Data, 1963) and Pines (Chem. Tech, 1982), which documents are incorporated by reference in their entirety herein. These molecules contain double and conjugated bonds in intricate structures containing a combination of cyclic and acyclic skeletons.

In practice, conjunct polymers are also called "red oils" due to their color and "acid-soluble oils" due to their high uptake in the catalyst phase where saturated hydrocarbons and paraffinic products are usually immiscible.

In one embodiment the control system controls the level of the conjunct polymer in the acidic ionic liquid catalyst in the alkylation reactor by adjusting an amount of catalyst regeneration. Examples of processes and reactors for regenerating catalysts by removing conjunct polymers from used acidic ionic liquid catalysts are described in the following patent publications: US20070142217A1, US2007014267A1, US20070142213A1, US20070142211A1, US20070142215A1, US200701412218A1, US20070142216A1, US20070249485A1, US20090253572A1, US20090170687A1, and US20090170688A1; and U.S. Pat. No. 7,651,970. The ionic liquid catalyst regenerator, for example, can comprise a reactive extraction column, the reactive extraction column comprising:

(a) an upper feed port, wherein a slurry of an ionic liquid catalyst enters the reactive extraction column bed packed with aluminum metal;
 (b) a lower feed port, wherein a solvent and optionally a hydrogen gas enter the reactive extraction column;
 (c) the bed comprised of the aluminum metal between the upper and lower feed ports, wherein the ionic liquid catalyst and the aluminum metal reacts to free conjunct polymers from the ionic liquid catalyst and some of the freed conjunct polymers are extracted from the ionic liquid catalyst by the solvent to provide regenerated ionic liquid catalyst;
 (d) a lower exit port, wherein the regenerated ionic liquid catalyst exits the reactive extraction column; and
 (e) an upper exit port, wherein the solvent and freed conjunct polymers exit the reactive extraction column. Ionic liquid catalyst regenerators having this design are described in US Patent Publication Number US20090170687A1.

In one embodiment, the control system controls the level of the conjunct polymer in the acidic ionic liquid catalyst in the alkylation reactor by adjusting the amount of a regenerated acidic ionic liquid catalyst that is recycled to the alkylation reactor.

The level of the halide containing additive can be controlled by adjusting the level of fresh halide containing additive or by controlling a level of the halide containing additive in a recycle stream to the alkylation reactor. Processes for controlling the level of the halide containing additive in a recycle stream are taught, for example in U.S. patent application Ser. No. 12/650,826, filed on Dec. 31, 2009.

In one embodiment, the level of the halide containing additive is controlled by a) stripping or distilling a hydrocarbon effluent from a reactor comprising an ionic liquid catalyst into a first fraction having at least 5 wt % of a hydrogen halide and a second fraction having less than 25 wppm of the hydrogen halide; and b) recycling at least a portion of the first fraction to the reactor to improve the selectivity of the products from the reactor to alkylate gasoline or middle distillate. In another embodiment, the control system that enables the alkylation reactor to operate in both an alkylate mode or a distillate mode receives information from an on-line HCl analyzer that measures the chloride content in an off-gas. The control system communicates changes to the operating conditions to maintain the chloride level in a predetermined range. Examples of how on-line HCl analyzers can be used in this process unit are described in U.S. patent application Ser. No. 12/233,41, filed on Sep. 18, 2008.

As described previously, the control system can be used to maintain the level of the conjunct polymer in the acidic ionic liquid catalyst at a lower level when it is operating in the alkylate mode. In one embodiment, the control system maintains the level of the conjunct polymer to at least 5 wt % lower when operating in the alkylate mode than when it is operating in the distillate mode.

In one embodiment, the control system controls both the level of the conjunct polymer in an ionic liquid catalyst in the alkylation reactor and the level of a halide containing additive in the alkylation reactor.

In some embodiments, gasoline blending components produced in either the alkylate mode or the distillate mode have low sulfur, such as less than 25 wppm, less than 20 wppm, less than 10 wppm, or less than 5 wppm. For example, the gasoline blending components can be produced in both modes having less than 25 wppm sulfur, less than 20 wppm sulfur, less than 10 wppm sulfur, or even less than 5 wppm sulfur.

The term "comprising" means including the elements or steps that are identified following that term, but any such elements or steps are not exhaustive, and an embodiment can include other elements or steps. For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

EXAMPLES

Example 1

A sample of N-butylpyridinium chloroaluminate ($C_5H_5C_4H_9Al_2Cl_7$) ionic liquid catalyst was analyzed and had the following elemental composition. The ionic liquid catalyst had aluminum chloride as the metal halide.

| | |
|---|---|
| Wt % Al | 12.4 |
| Wt % Cl | 56.5 |
| Wt % C | 24.6 |
| Wt % H | 3.2 |
| Wt % N | 3.3 |

Example 2

"Gasoline Mode"

The ionic liquid catalyst described in Example 1 was used to alkylate $C_4$ olefins with isobutane in a process unit. The alkylation was performed in a continuously stirred tank reactor (CSTR). An 8:1 molar ratio of isobutane to total olefin mixture was fed to the reactor via a first inlet port while vigorously stirring at approximately 1600 RPM. The ionic liquid catalyst was fed to the reactor via a second inlet port, targeting to occupy 6 vol % in the reactor. A small amount of anhydrous t-butyl chloride, corresponding to 60:1 molar ratio of feed olefin to butyl chloride, was added to the ionic liquid catalyst in the reactor. The average residence time of the combined feeds (isobutane/olefin mixture and catalyst) in the reactor was about four minutes. The outlet pressure was maintained at 200 psig and the reactor temperature was maintained at 15.6° C. (60° F.) using external cooling. The reactor effluent was separated with a coalescing separator into a hydrocarbon phase and an ionic liquid catalyst phase.

A portion of the separated ionic liquid catalyst phase was sent to a catalyst regeneration unit containing aluminum pellets. The catalyst regeneration unit comprised a regeneration reactor that was adjusted within a range from 76.7 to 110° C. (170 to 230° F.) to maintain the conjunct polymer level in the alkylation catalyst from 5 to 10 wt %.

The hydrocarbon phase was then sent to a series of three distillation columns to separate $C_5^+$, n-butane, $C_3^-$ offgas and isobutene recycle streams. The $C_5^+$ stream was analyzed using gas chromatography for detailed hydrocarbon analysis and D86 laboratory distillation. Research Octane number was calculated based on GC composition and Research Octane number of pure compounds assuming volumetric linear blending. The resulting $C_5^+$ stream was an alkylate gasoline having a 95 RON. ASTM D86 distillation of the $C_5^+$ stream showed the initial boiling point of 86° F. (30 degree Celsius), $T_{50}$ boiling point of 223° F. (106.1 degree Celsius), $T_{90}$ boiling point of 284° F. (140 degree Celsius) and the end boiling point of 404° F. (206.7 degree Celsius). These results indicated that the process generated high quality alkylate gasoline that can be readily blended to the refinery gasoline pool.

Example 3

"Distillate Mode"

Experimental conditions that were nearly identical to those of Example 2 were followed, except that the regeneration temperature was adjusted to allow the conjunct polymer level in the alkylation catalyst to be maintained at a higher level of about 20 wt %.

As in Example 2, the hydrocarbon phase was sent to a series of three distillation columns to separate $C_5^+$, n-butane, $C_3^-$ offgas and isobutene recycle streams. The $C_5^+$ stream was analyzed using the ASTM D2887 SimDist chromatography method. D2887 SimDist results showed $T_{10}$ boiling point of 73° F. (22.78 degree Celsius) (contains some light material), $T_{50}$ point of 343° F. (172.8 degree Celsius), $T_{90}$ point of 648° F. (342.2 degree Celsius) and the end point of 873° F. (467.2 degree Celsius). Weight percent yields of hydrocarbon fuel product streams were estimated using the GC data and results are summarized in Table 1.

TABLE 1

Estimated $C_5^+$ Product Distribution for "Distillate Mode"

| | wt % | vol % | density |
|---|---|---|---|
| Naphtha, C5-280 F | 34.1 | 36.8 | 0.70 |
| Light distillate, 280 F-500 F | 33.2 | 32.6 | 0.77 |
| Heavy distillate, 500 F-EP | 32.7 | 30.5 | 0.81 |
| Sum, % | 100.0 | 100.0 | |

Results in Examples 1 and 2 demonstrate that for the "Gasoline Mode", essentially all, about 100%, of the $C_5^+$ stream is gasoline boiling range material. For the "Distillate Mode", about 60+wt % of the $C_5^+$ stream is distillate material boiling in the range of either light distillate (kerosene and jet) or heavy distillate (diesel).

The process unit was operated in the "distillate mode" for one week. Then the used catalyst was drained and fresh catalyst was added to make the conjunct polymer level of the blend alkylation catalyst to be at about 5-10 wt % conjunct polymer. Once the level of conjunct polymer level in the alkylation catalyst was reduced to be within about 5 to 10 wt %, the $C_5^+$ stream became lighter boiling range material alkylate gasoline. This change back from "distillate mode" to "alkylate mode" occurred within two days.

Example 4

Product Properties of Alkylate Gasoline and Distillate Using $C_4$ Olefin/Isobutane Feeds in "Distillate Mode"

The $C_5^+$ stream from Example 3 was distilled in a laboratory into gasoline, light distillate (kerosene and jet) and heavy distillate (diesel) fractions. Product properties of each fraction are summarized in Table 2.

TABLE 2

Product Properties of Gasoline and Distillate Streams

| Gasoline Properties | |
| --- | --- |
| F-1 Research Octane (RON) | 95 |
| F-2 Motor Octane (MON) | 91 |
| Specific Gravity, g/cc | 0.70 |
| Reid Vapor Pressure | 3.6 |
| Sulfur, ppm | 3 |
| Light Distillate Properties, as produced | |
| Flash point, °F. | ~100 |
| Freeze point, °F. | <−76 |
| Cloud point, °F. | <−76 |
| Cetane number | ~30 |
| Bromine number | ~70 |
| Specific Gravity, g/cc | 0.77 |
| Sulfur, ppm | 3 |
| Heavy Distillate Properties, as produced | |
| Freeze point, °F. | <−76 |
| Cloud point, °F. | <−76 |
| Cetane number | ~30 |
| Bromine number | ~60 |
| Specific Gravity, g/cc | 0.82 |
| Sulfur, ppm | 18 |

The product property data indicated the process makes very high quality alkylate gasoline with excellent octane numbers, low vapor pressure, and low sulfur.

Additionally, the distillate fractions showed excellent freeze and cloud points, indicating these streams can be used to improve the characteristics of kerosene, jet, or diesel blends. The light and heavy distillate fractions showed 60-70 Bromine numbers indicating the fractions contain unsaturated olefins. Thus it can be desirable to send these streams to a hydrotreating unit to saturate the olefins and to remove any other undesirable impurities.

What is claimed is:

1. An alkylation process unit, comprising: a control system, connected to an alkylation reactor, that is configured to enable the alkylation reactor to operate in both:
   a. an alkylate mode that produces a gasoline blending component having a RON of 90 or higher and having greater than 50 wt % of a C5+ hydrocarbon stream that boils at 137.8° C. or below; and
   b. a distillate mode that produces:
      i. a second gasoline blending component having a second RON of 85 or higher and
      ii. a distillate product that boils above 137.8° C.;
   wherein the control system is configured to control a level of a conjunct polymer and wherein the control system comprises a catalyst regenerator.

2. The alkylation process unit of claim 1, wherein the control system controls the level of the conjunct polymer in an acidic ionic liquid catalyst in the alkylation reactor.

3. The alkylation process unit of claim 2, wherein the control system is configured to adjust an amount of catalyst regeneration.

4. The alkylation process unit of claim 2, wherein the control system is configured to maintain the level of the conjunct polymer in the acidic ionic liquid catalyst at a lower level when the alkylation reactor is operating in the alkylate mode.

5. The alkylation process unit of claim 4, wherein the lower level is 5 to 10 wt %.

6. The alkylation process unit of claim 4, wherein the level of the conjunct polymer is at least 5 wt % lower when operating in the alkylate mode than when the alkylation process unit is operating in the distillate mode.

7. The alkylation process unit of claim 1, wherein the control system is configured to adjust an amount of a regenerated acidic ionic liquid catalyst that is recycled to the alkylation reactor.

8. The alkylation process unit of claim 1, wherein the control system is configured to control both the level of the conjunct polymer in an ionic liquid catalyst in the alkylation reactor and a level of a halide containing additive in the alkylation reactor.

9. The alkylation process unit of claim 1, wherein the control system is configured to switch back and forth from enabling the alkylation reactor to operate in the alkylate mode to enabling the alkylation reactor to operate in the distillate mode.

10. The alkylation process unit of claim 9, wherein a time between operating in the alkylate mode and operating in the distillate mode is a week or less.

11. The alkylation process unit of claim 1, wherein the control system is configured to adjust a reaction temperature in the alkylation reactor from −40° C. to 100° C. in the alkylate mode and to a higher reaction temperature in the distillate mode.

12. The alkylation process unit of claim 1, wherein the control system is configured to adjust a reaction temperature in the alkylation reactor to be approximately the same while operating in the alkylate mode and the distillate mode.

13. The alkylation process unit of claim 1, wherein the control system is configured to control a level of a halide containing additive in the alkylation reactor.

14. The alkylation process unit of claim 13, wherein the level of the halide containing additive is controlled by a) stripping or distilling a hydrocarbon effluent from the alkylation reactor and producing a fraction having at least 5 wt % of a hydrogen halide, and b) recycling at least a portion of the fraction to the alkylation reactor.

15. The alkylation process unit of claim 4, wherein the lower level is less than 10 wt % and a higher level of the conjunct polymer when the alkylation reactor is operating in the distillate mode is from above 10 wt % to 40 wt %.

16. The alkylation process unit of claim 15, wherein the higher level is above 15 wt %.

17. The alkylation process unit of claim 1, wherein the acidic ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof.

18. An alkylation process unit, comprising: a control system that comprises an ionic liquid catalyst regenerator, connected to an alkylation reactor, that is configured to enable the alkylation reactor to operate in both:
   a. an alkylate mode that produces a gasoline blending component having a RON of 90 or higher and greater than 50 wt % of a C5+ hydrocarbon stream that boils at 137.8° C. or below; and
   b. a distillate mode that produces both:
      i. a second gasoline blending component having a second RON of 85 or higher and
      ii. a distillate product that boils above 137.8° C.; and
   wherein the ionic liquid catalyst regenerator maintains a level of a conjunct polymer in an acidic ionic liquid catalyst in the alkylation reactor at a lower level when the alkylation reactor is operating in the alkylate mode and at a higher level when the alkylation reactor is operating in the distillate mode.

19. A process unit, comprising a control system connected to a reactor that is configured to enable the reactor to operate:
 a. in an alkylate mode that produces a gasoline blending component having: a RON of 90 or higher, a RVP of 7 psi (4.826e+004 newtons/square meter) or less, and a level of sulfur less than 10 wppm, and
 b. in a distillate mode that produces a second gasoline blending component having a RON of 85 or higher, a RVP of 7 psi (4.826e+004 newtons/square meter) or less and a distillate product having a freeze point less than −60° C. (−76 degree Fahrenheit), a cloud point less than −60° C. (−76 degree Fahrenheit), and a cetane number of about 30;
wherein the control system comprises a catalyst regenerator.

* * * * *